(12) United States Patent
Niver

(10) Patent No.: US 11,272,967 B2
(45) Date of Patent: Mar. 15, 2022

(54) BONE PLATE SYSTEM AND METHOD

(71) Applicant: Medline Industries, LP, Northfield, IL (US)

(72) Inventor: Ryan Niver, Glenview, IL (US)

(73) Assignee: Medline Industries, LP, Northfield, IL (US)

( * ) Notice: Subject to any disclaimer, the term of this patent is extended or adjusted under 35 U.S.C. 154(b) by 301 days.

(21) Appl. No.: 16/507,630

(22) Filed: Jul. 10, 2019

(65) Prior Publication Data

US 2020/0015871 A1 Jan. 16, 2020

Related U.S. Application Data

(60) Provisional application No. 62/696,643, filed on Jul. 11, 2018.

(51) Int. Cl.
*A61B 17/80* (2006.01)
*A61B 17/86* (2006.01)
*A61B 17/56* (2006.01)

(52) U.S. Cl.
CPC ...... *A61B 17/8057* (2013.01); *A61B 17/8004* (2013.01); *A61B 17/86* (2013.01); *A61B 2017/564* (2013.01)

(58) Field of Classification Search
CPC ............ A61B 17/8052; A61B 17/8057; A61B 17/8014
See application file for complete search history.

(56) References Cited

U.S. PATENT DOCUMENTS

| 5,709,686 | A  | 1/1998  | Talos     |
|-----------|----|---------|-----------|
| 6,454,769 | B2 | 9/2002  | Wagner    |
| 6,821,278 | B2 | 11/2004 | Frigg     |
| 6,955,677 | B2 | 10/2005 | Dahners   |
| 7,309,340 | B2 | 12/2007 | Fallin    |
| 7,955,364 | B2 | 6/2011  | Ziolo     |
| 8,343,196 | B2 | 1/2013  | Schneider |

(Continued)

FOREIGN PATENT DOCUMENTS

| DE | 4343117    | 6/1995 |
|----|------------|--------|
| WO | 2005018472 | 3/2005 |

OTHER PUBLICATIONS

Osteomed, "ExtremiLock Foot Plating System," published prior to 2017.

(Continued)

*Primary Examiner* — Olivia C Chang
(74) *Attorney, Agent, or Firm* — Fitch, Even, Tabin & Flannery LLP

(57) ABSTRACT

A bone plate system comprises a bone screw and a bone plate having at least two screw-receiving hole structures, at least one of the hole structures comprising an eccentric portion adjacent a first seating area for biasing bone in an inferior fusion area into dynamic compression as the screw is advanced, and a cowl portion that at least partially defines a second seating area and being positioned to enable cross-screw compression of an inferior fusion area. The screw is seatable in either the first or second seating area at the option of a surgeon. A surgical method generally comprises inserting a bone screw into the compression plate and compressing bone in an inferior fusion area by either dynamic or cross-screw compression.

20 Claims, 13 Drawing Sheets

(56) References Cited

U.S. PATENT DOCUMENTS

| | | |
|---|---|---|
| 8,529,608 B2 | 9/2013 | Terrill |
| 8,845,698 B2 | 9/2014 | Schneider |
| 8,852,245 B2 | 10/2014 | Schneider |
| 8,876,873 B2 | 11/2014 | Schneider |
| 8,906,076 B2 | 12/2014 | Mocanu |
| 9,011,540 B1 | 4/2015 | Castro |
| 9,295,505 B2 | 3/2016 | Schneider |
| 9,351,776 B2 | 5/2016 | Terrill |
| 9,468,479 B2 | 10/2016 | Marotta |
| 9,486,264 B2 | 11/2016 | Reiley |
| 9,492,201 B2 | 11/2016 | Reiley |
| 9,662,157 B2 | 5/2017 | Schneider |
| 9,763,716 B2 | 9/2017 | Terrill |
| 9,839,448 B2 | 12/2017 | Reckling |
| 9,936,983 B2 | 4/2018 | Mesiwala |
| 9,949,843 B2 | 4/2018 | Reiley |
| 10,166,033 B2 | 1/2019 | Reiley |
| 10,201,427 B2 | 2/2019 | Mauldin |
| 10,245,085 B2 | 4/2019 | Terrill |
| 10,245,086 B2 | 4/2019 | Treace |
| 10,245,088 B2 | 4/2019 | Dayton |
| 10,363,140 B2 | 7/2019 | Mauldin |
| 10,376,206 B2 | 8/2019 | Sand |
| 2011/0009866 A1* | 1/2011 | Johnson ............. A61B 17/8052 606/70 |
| 2012/0123484 A1* | 5/2012 | Lietz .................... A61B 17/151 606/281 |

OTHER PUBLICATIONS

Stryker, "Stryker Foot & Ankle Plating Systems," Operative Technique Anchorage 2 CP, 2016.

\* cited by examiner

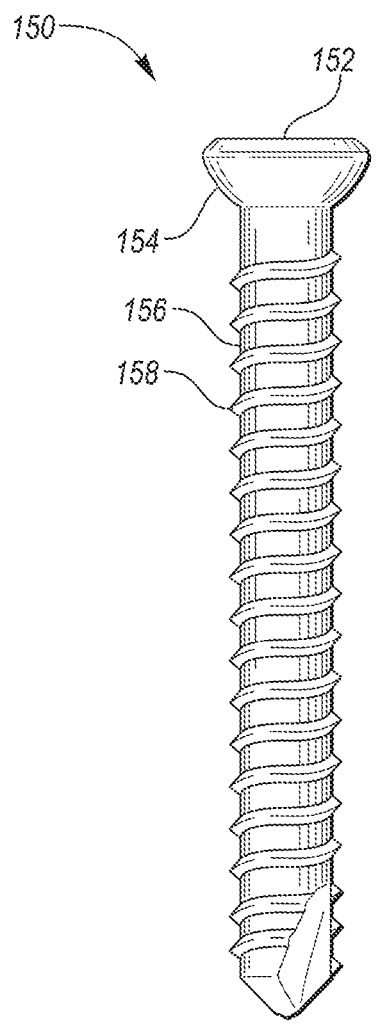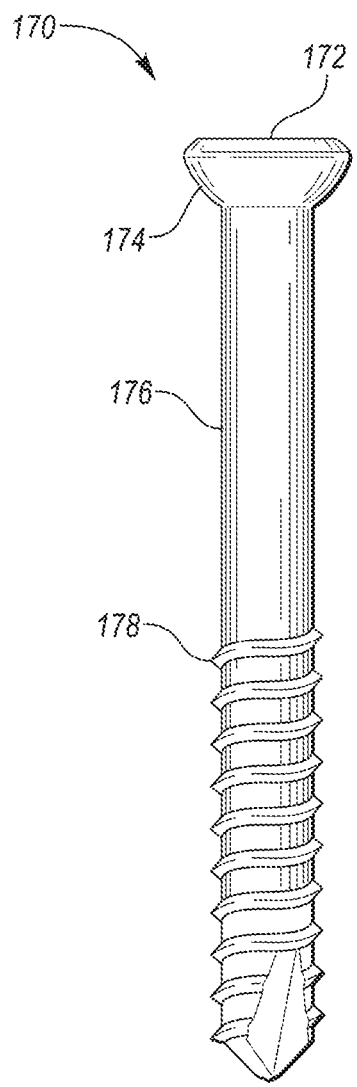
FIG. 10
FIG. 11

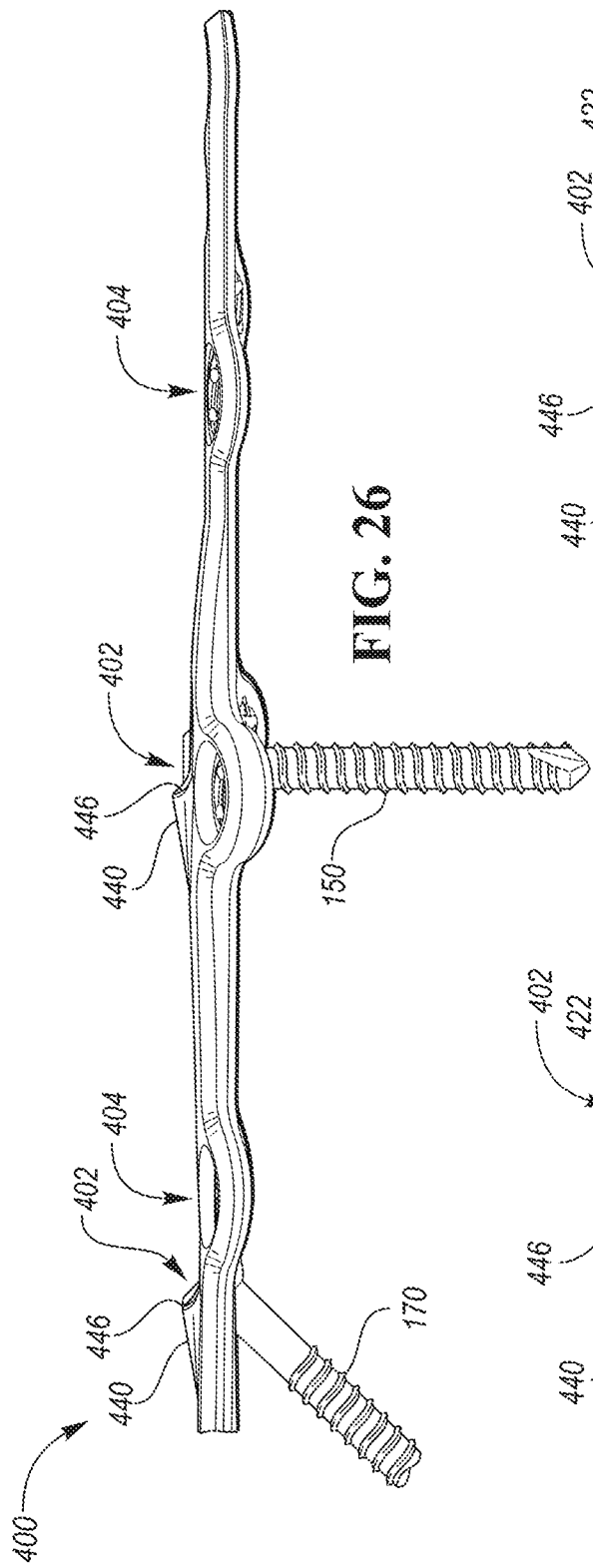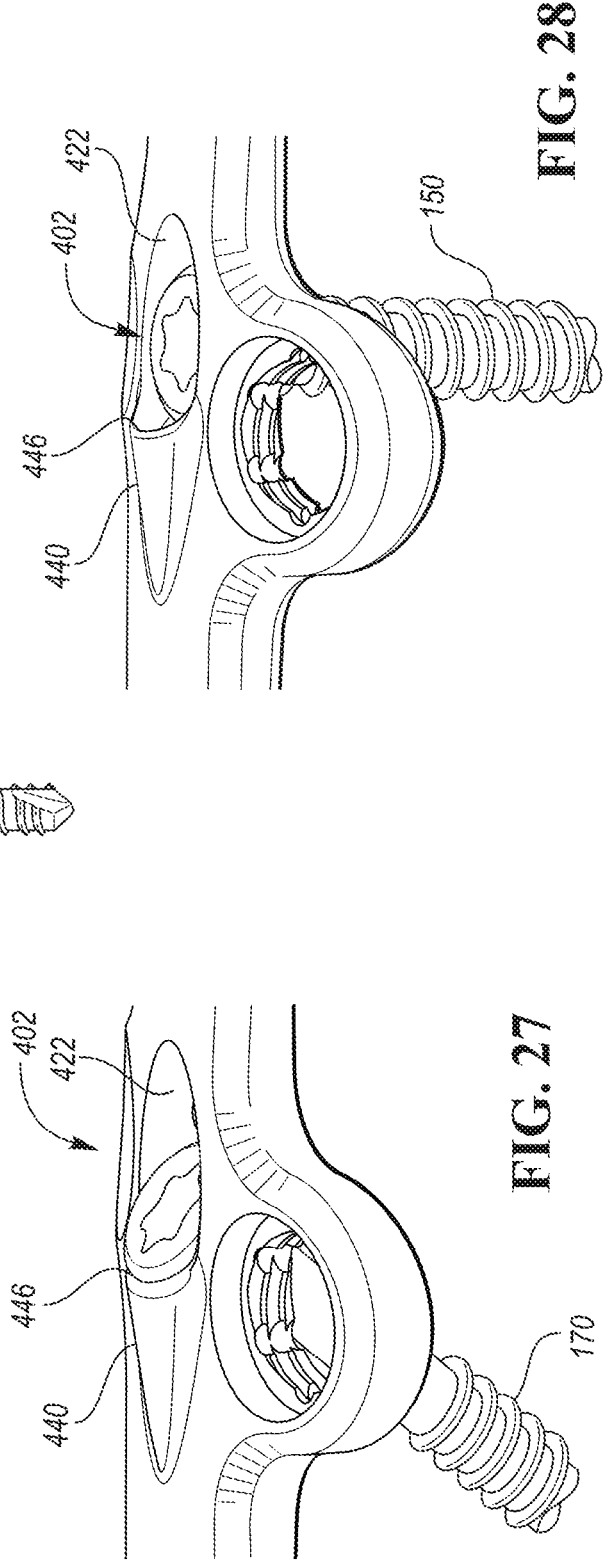

BONE PLATE SYSTEM AND METHOD

CROSS-REFERENCE TO RELATED APPLICATIONS

This application claims the benefit of U.S. Provisional Application No. 62/696,643, filed Jul. 11, 2018, which is hereby incorporated by reference as if fully set forth herein.

TECHNICAL FIELD

This disclosure generally relates to bone plates for use in bone fusion procedures, and more particularly, to bone plates for fusion of two bone structures or repair of a bone fracture via bone compression plates.

BACKGROUND

Numerous forms of bone fusion are known in the art. Many plating systems have incorporated compression features to cause compression of a bone fusion area, by which is contemplated a fracture or joint to be fused. Plates designed for dynamic compression incorporate at least one screw hole at one portion of the plate and a compression slot disposed at a different portion of the plate. The compression slot comprises a hole with an eccentric feature that generally is sloped inferiorly towards the direction of the other hole. After driving a screw into inferior bone through the non-compression screw hole, a screw then is driven through the compression slot. An inferior side of the head end engages the eccentric feature, which thereby creates a camming interaction between the screw and the eccentric feature to pull the underlying bone segments towards one another as the screw travels laterally relative down the slope of the eccentric feature. As the head of the screw moves to its fully seated position, and with the other screw already drilled in place, the bone fusion area will be compressed via dynamic compression.

It is also known in the art to employ cross-plate screw compression. With this type of plate, a user places a screw through a plate at a trajectory that allows the screw to reach across the joint or fracture in the inferior fusion area. The plate effectively becomes a large washer-like structure, such that, as the threads of the screw engage the bone on the far side of the fracture or joint, the advancement of the screw causes compression across the bone fusion area.

SUMMARY

A bone plate system comprising at least a first bone screw and a bone plate has been devised. The bone plate has at least two screw-receiving hole structures defining respectively a first hole and a second hole. At least one of the hole structures includes an eccentric portion adjacent a first seating area, the head of the first screw being shaped to engage the eccentric portion and via camming action to bias bone in an inferior fusion area into dynamic compression as the screw is advanced, the first screw being positioned at a first orientation when seated in the first seating area. The same hole structure comprises a hood or cowl portion that at least partially defines a second seating area. The second seating area is positioned with respect to the first area such that the first screw is positioned at a second orientation when the first screw is seated in the second seating area. The second orientation is different from the first orientation and the first screw is sized to enable cross-screw compression of the inferior fusion area. The first screw is seatable in either the first seating area or the second seating area at the option of the surgeon. This approach enables the surgeon to select either dynamic compression or cross-screw compression using the same bone plate system, depending on the judgment of the surgeon.

BRIEF DESCRIPTION OF THE DRAWINGS

FIG. 10 is a side elevation view of a first bone screw.

FIG. 11 is a side elevation view of a second bone screw.

FIG. 26 is a side elevation view of a portion of the fourth bone plate including the first bone screw of FIG. 10 and the second bone screw of FIG. 11 assembled with the fourth bone plate.

FIG. 27 is a top perspective view of the fourth bone plate showing the second bone screw of FIG. 11 assembled with the fourth bone plate FIG. 28 is a top perspective view of the fourth bone plate showing the first bone screw of FIG. 10 assembled with the fourth bone plate.

Terms of orientation and relative position (such as "inferior") are not intended to limit the position or orientation of the bone plate or system described herein.

DETAILED DESCRIPTION

Embodiments of the present disclosure are described herein. It is to be understood, however, that the disclosed embodiments are merely examples and other embodiments may take various and alternative forms. The figures are not necessarily to scale; some features could be exaggerated or minimized to show details of particular components. Therefore, specific structural and functional details disclosed herein are not to be interpreted as limiting, but merely as a representative basis for teaching one skilled in the art to variously employ the present invention. As those of ordinary skill in the art will understand, various features illustrated and described with reference to any one of the figures may be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

Figure 1:
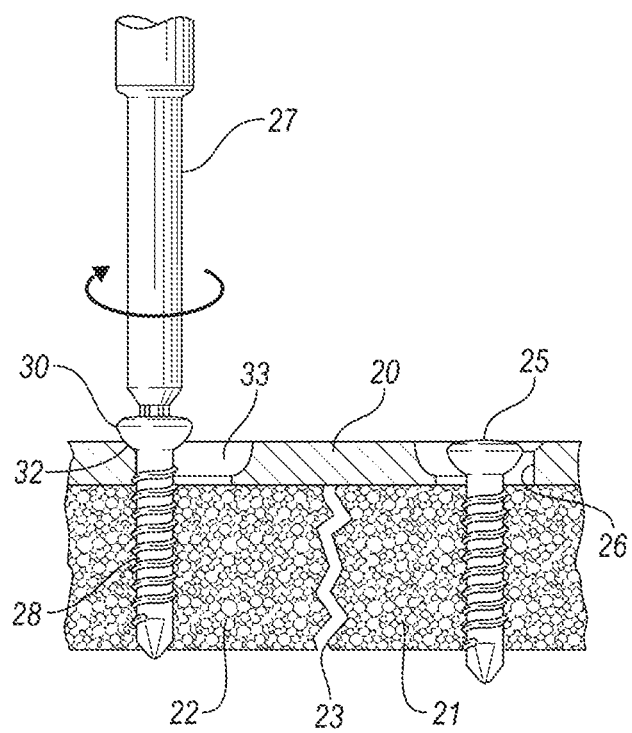
FIGS. 1 and 2 are representational views of prior art dynamic compression bone plate systems, FIG. 1 illustrating initial placement and drilling of the screw into a compression slot, and FIG. 2 illustrating the screw once advanced to the fully seated position.
Figure 2:
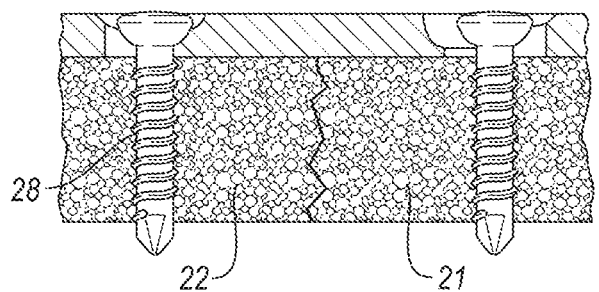

With reference now to FIG. 1, the bone plate 20 covers the inferior bone fusion area of a patient as illustrated via bone sections 21, 22. The patient's bone has a fracture 23. After screwing a first bone screw 25 into a first hole 26 and into bone section 21, a driver 27 is used to screw a second bone screw 28 into the patient's bone section 22 at the other side of the fracture 23. As seen, the inferior portion of the screw head 30 engages an eccentric ramp surface 32 of the compression slot 33, causing the plate and screw construct (20 and 25) to pull towards the compression screw 28, thus creating compression. When the screw 28 reaches its fully seated position, as shown in FIG. 2, the bone portions 21, 22 abut one another to aid in healing.

Figure 3:
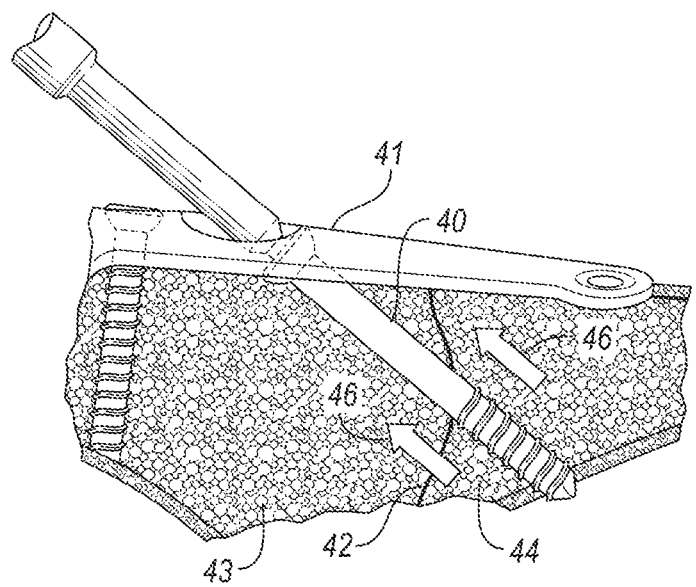
FIG. 3 is a representational view illustrating a prior art cross-screw compression system.
Figure 4:
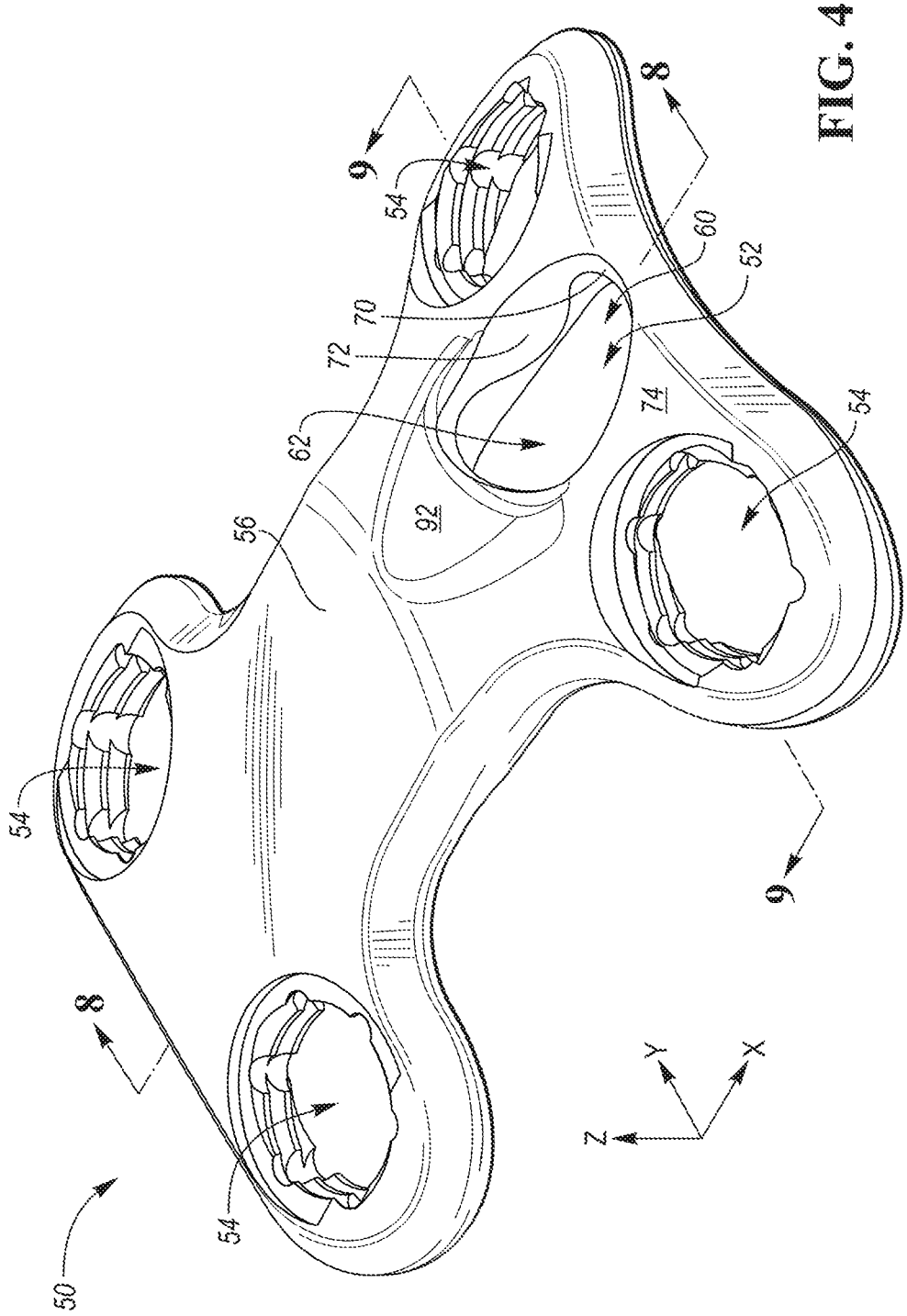
FIG. 4 is a top perspective view of a first bone plate.
Figure 5:
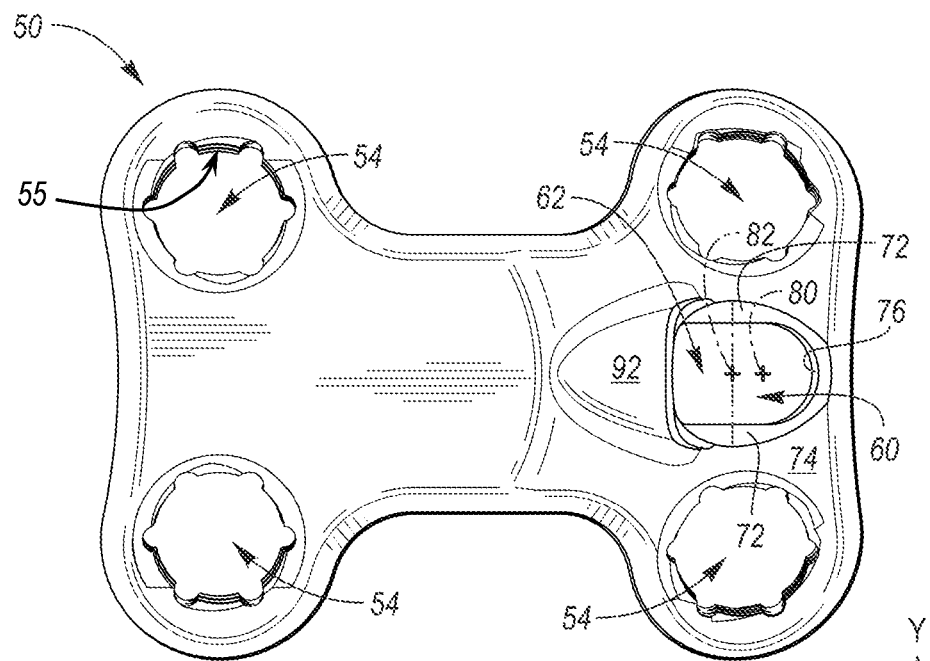
FIG. 5 is a top plan view of the first bone plate.
Figure 6:
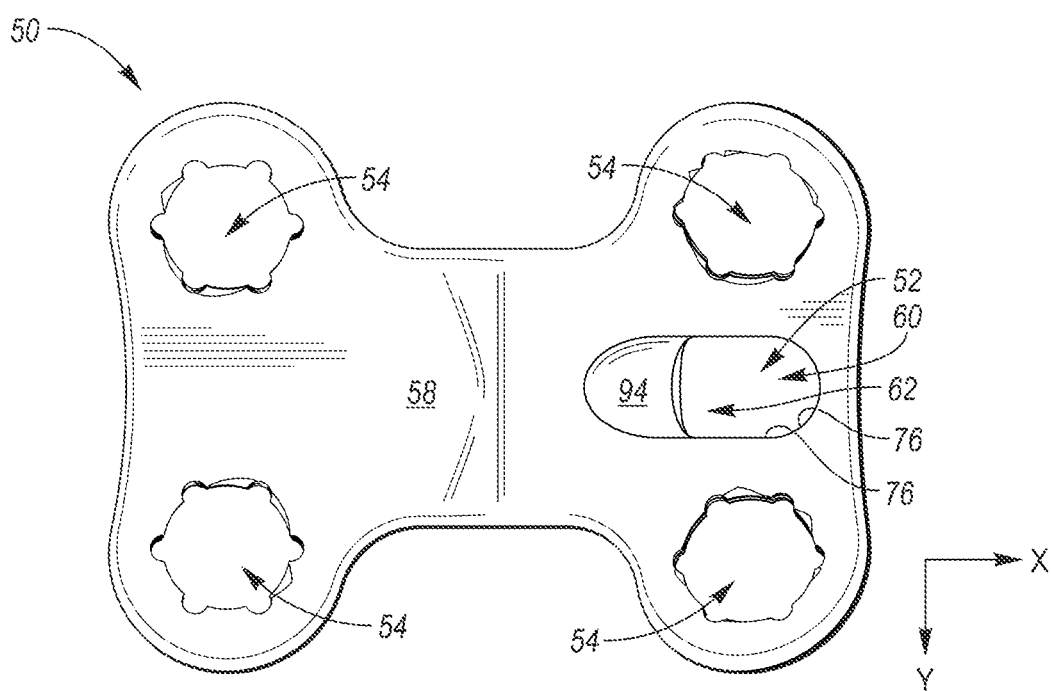
FIG. 6 is a bottom plan view of the first bone plate.

As illustrated in FIG. 3, the illustrated screw 40 is driven through the plate 41 and into the inferior fusion area, specifically through bone portions 43, 44 on both sides of the fracture 42. As the screw 40 is advanced through the second portion 44 of the bone, the bone will retract in the direction of arrows 46, thus again causing abutment of the bone portions 43, 44 in the inferior fusion area.

Turning now to FIGS. 4-9, a bone plate 50 with a first hole structure 52 is shown. The first hole structure 52 may be referred to as a "combination" hole structure 52, or a "dual mode compression" hole structure.

The bone plate 50 may also include at least one second hole structure. For example, the depicted bone plate 50 includes four locking hole structures 54 disposed through four lobes of the bone plate 50, with the combination hole structure 52 extending through the bone plate 50 between two of the locking hole structures 54. A medial plate region 56 may extend between first and second pairs of the locking hole structures 54. As used herein, a "medial" plate region may be a body portion (which may be an elongated body portion) of a bone plate that is situated near the midline or median plane of the bone plate.

The locking hole structures 54 include thread-engaging portions 55, which, in the illustrated embodiment, take the form of broken threads or lugs. Alternatively, these hole structures may include one or more interior unbroken threads (not shown). Furthermore, although shown as having common interior geometries, the locking hole structures 54 may have different interior geometries.

The bone plate 50 may be, for example, a talonavicular fusion plate that, following a surgical procedure, fuses the talus bone of the hindfoot and the navicular bone of the midfoot.

The combination hole structure 52 permits a practitioner to choose among a plurality of bone screw varieties to be inserted into the combination hole structure 52. As will be appreciated, a practitioner may opt to orient a first bone screw, such as a dynamic compression screw, at a first orientation through the combination hole structure 52, or may opt to orient a second bone screw, such as an interfragmentary compression screw, at a second orientation through the combination hole structure 52 that is different than the first orientation.

In this way, the combination hole structure 52 includes a first seating area, shown generally at 60, and a second seating area, shown generally at 62, that is at least partially offset from the first seating area 60. The first seating area 60 is configured to receive a dynamic compression screw, and the second seating area 62 is configured to receive an interfragmentary compression screw. Both seating areas are unthreaded in this embodiment, although it is contemplated that the combination hole structure may in other embodiments include a threaded or thread-engaging structure for one or both of the positions of the screw.

More particularly, the combination hole structure 52 includes a ramp wall 70, which may be referred to as an eccentric portion, and curved side walls 72 that extend about at least a portion of the first seating area 60 and that may be referred to as generally bowl-shaped curved side walls 72.

The curved side walls 72 extends continuously from the ramp wall 70. The ramp wall 70 and curved side walls 72 generally slope inwardly (e.g., toward a central axis of the combination hole structure 52) as the walls extend away from an upper surface 74 of the bone plate 50 in a direction of bone screw insertion (e.g., in a direction of the Z axis). In this way, the ramp wall 70 generally slopes in a direction toward the second seating area 62, and the curved side walls 72 generally slope toward each other.

The ramp wall 70 may generally extend about a first axis, which may be referred to as an insertion axis 80, that extends orthogonal to the X-Y plane. The curved side walls 72 may generally extend about a second axis. The second axis, which also extends orthogonal to the X-Y plane, may be referred to as a seating axis 82. As shown, the seating axis 82 may be offset from the insertion axis 80; for example, along a direction of the X axis. The curved side walls 72 may cooperate to define a generally bowl-shaped first seating area 60. In this way, the curved side walls 72 may taper relative to the seating axis 82, and upper portions of the curved side walls 72 (e.g., proximate the upper surface 74) curve about the seating axis 82.

As discussed in greater detail elsewhere herein, the ramp wall 70 and the curved side walls 72 cooperate to facilitate insertion of a dynamic compression screw in the first seating area 60.

Figure 8:
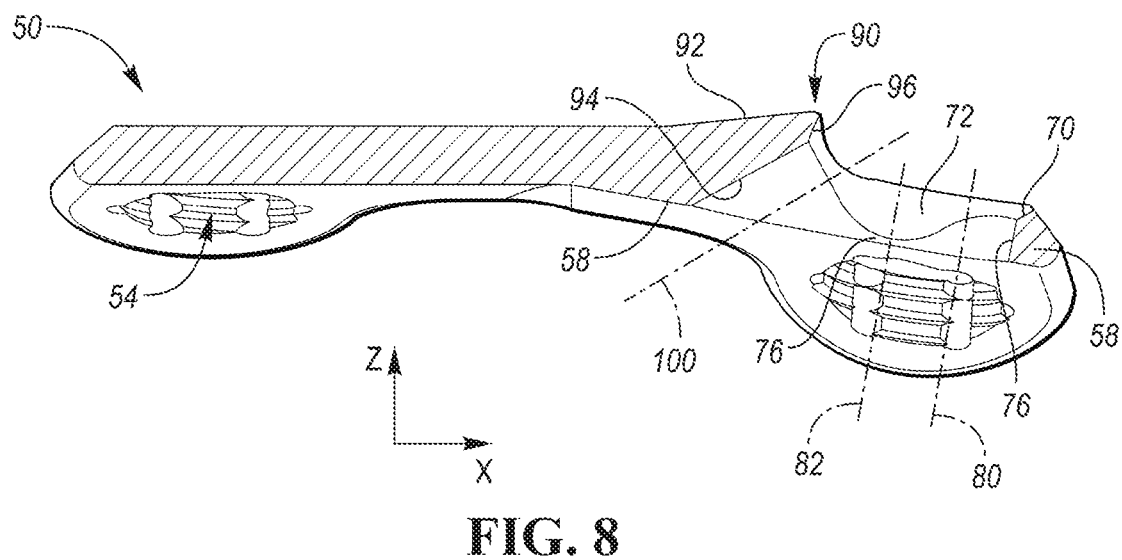
FIG. 8 is a cross-sectional view of the first bone plate taken along the line 8-8 of FIG. 4.
Figure 9:
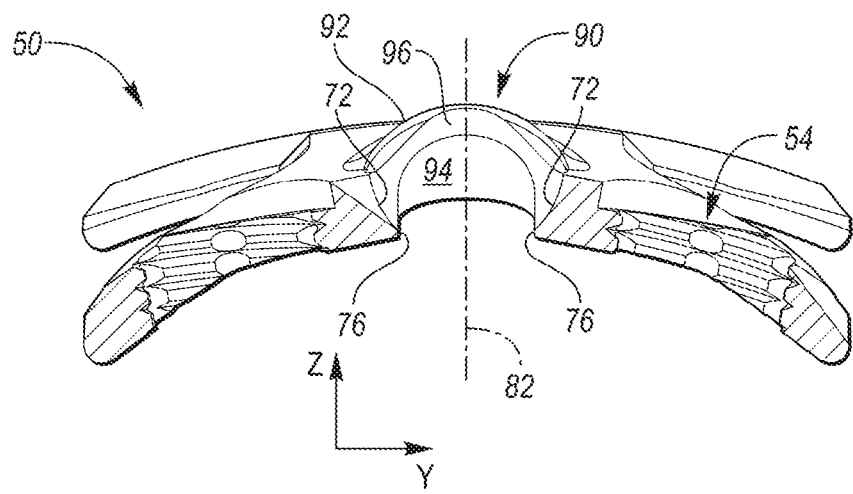
FIG. 9 is a cross-sectional view of the first bone plate taken along the line 9-9 of FIG. 4.

As shown in FIG. 8, a non-tapering wall 76 (which may be a generally cylindrical wall) extends below one or both of the ramp wall 70 and the curved side walls 72. More particularly, the non-tapering wall 76 includes a portion that extends from the ramp wall 70 to the lower surface 58 of the bone plate 50. The non-tapering wall 76 further include portions that extend from the curved side walls 70 to the lower surface 58 of the bone plate 50.

The bone plate 50 further includes a hood or cowl 90 that at least in part defines the second seating area 62. At least a portion of the cowl 90 is contiguous with the curved side walls 72.

The cowl 90 includes an upper cowl surface 92 and a lower cowl surface 94 opposite the upper cowl surface 92. At least a portion of the upper cowl surface 92 is elevated (e.g., in the Z direction) relative to the upper surface 74 of the bone plate 50 proximate the curved side walls 72.

The cowl 90 may include a cowl abutment surface 96 that extends between the upper cowl surface 92 and the lower cowl surface 94. The cowl abutment surface 96 extends obliquely relative to one or both of the upper cowl surface 92 and the lower cowl surface 94. The cowl abutment surface 96 extends continuously from one or both of the curved side walls 72

Figure 7:
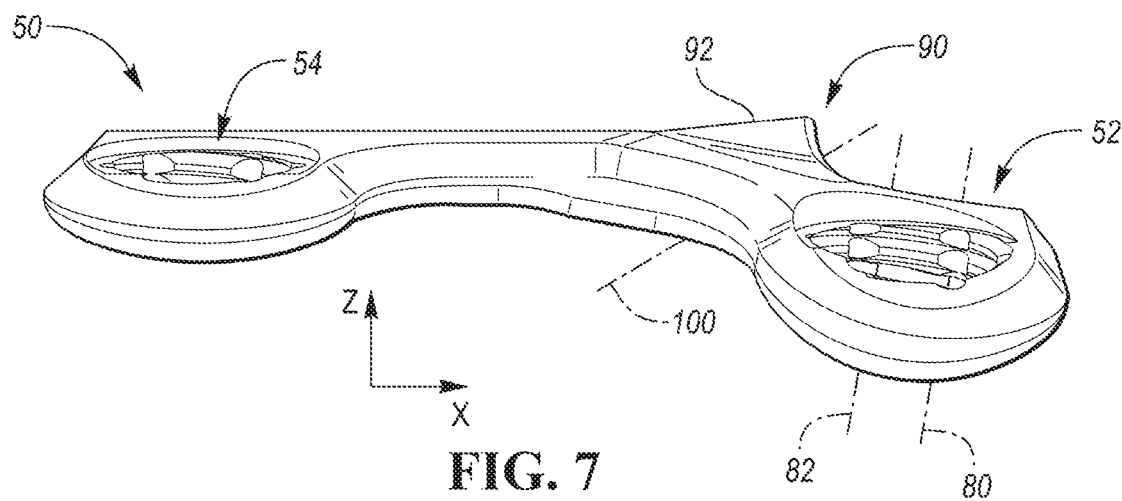
FIG. 7 is a side elevation view of the first bone plate.

As shown in FIGS. 7 and 8, the lower cowl surface 94 extends about a cross-plate axis 100. The cross-plate axis 100 extends obliquely relative to one or both of the insertion axis 80 and the seating axis 82.

According to one aspect, no structure or portion of the combination hole structure 52 extends below the lower surface 58 of the bone plate 50. As such, the lower surface of the bone plate 50 may be disposed adjacent to (e.g., in direct contact with) an inferior bone structure about an entire lower perimeter of the combination hole structure 52.

Referring to FIG. 10, a first bone screw is shown. The first bone screw may be a dynamic compression bone screw 150. The dynamic compression bone screw 150 includes a screw head 152 that includes an inferior portion 154. A shaft 156 of the dynamic compression bone screw 150 includes threads 158 that extends along at least half of the length of the shaft 156. In another aspect, the threads 158 may extend along less than half of the length of the shaft 156.

Referring to FIG. 11, a second bone screw is shown. The second bone screw may be an interfragmentary compression bone screw 170. The interfragmentary compression bone screw 170 includes a screw head 172 that includes an inferior portion 174. A shaft 176 of the interfragmentary compression bone screw 170 includes threads 178 that extends along less than half of the length of the shaft 176. In another aspect, the threads 178 may extend along at least half of the length of the shaft 176.

Figure 12:
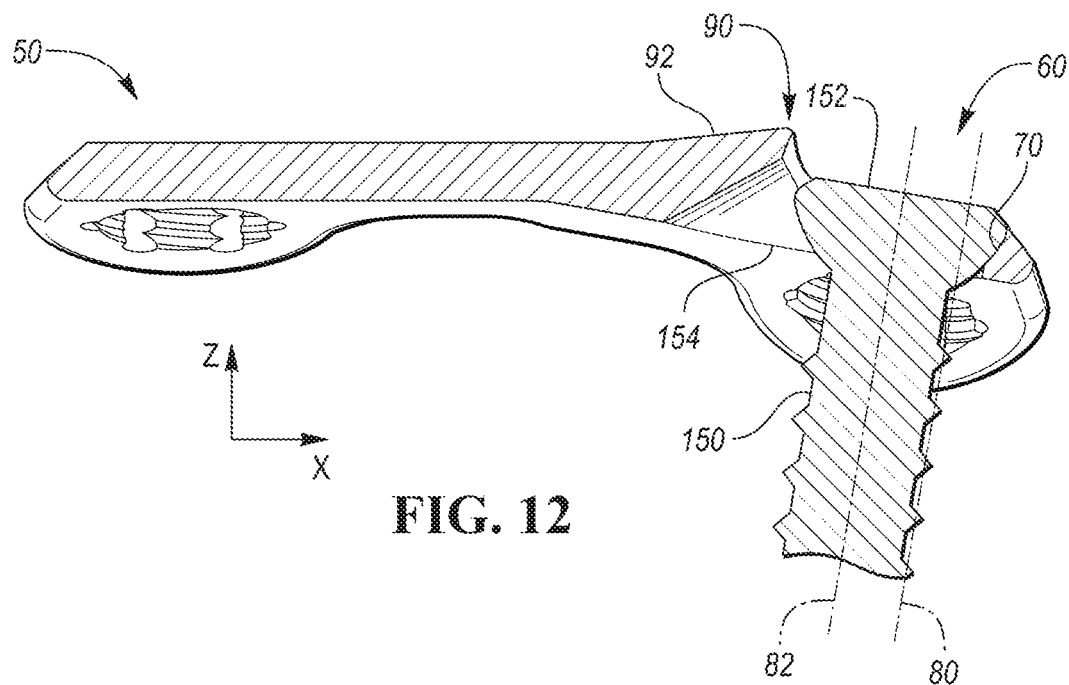
FIG. 12 is a cross-sectional view of FIG. 8 showing a portion of the first bone screw of FIG. 10 assembled with the first bone plate.

Referring to FIG. 12, the dynamic compression bone screw 150 is inserted into the first seating area 60. More particularly, the dynamic compression bone screw 150 is initially inserted along insertion axis 80. At this position, the inferior portion 154 of the screw head 152 engages the ramp wall 70. As the dynamic compression bone screw 150 is driven into the bone (e.g., along a direction of the Z axis), the inferior portion 154 slides down the ramp wall 70, and concurrently slides horizontally (e.g., along a direction of the X axis) toward the seating axis 82. As such, via camming action between the inferior portion 154 and the ramp wall 70, the dynamic compression bone screw 150 causes relative lateral movement of the underlying bone portions of the inferior fusion area to thereby bring them into abutment with one another. Upon installation, at least a portion of the screw head 152 may extend at least partially beneath a portion of the cowl 90 (e.g., inferior to the cowl abutment surface 96).

Figure 13:
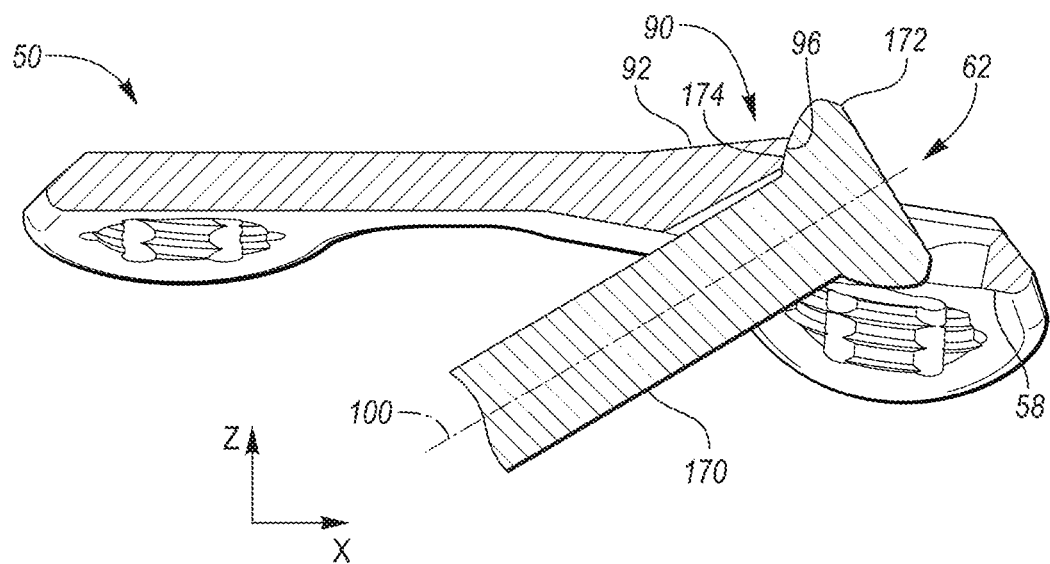
FIG. 13 is a cross-sectional view of FIG. 8 showing a portion of the second bone screw of FIG. 11 assembled with the first bone plate.

Referring to FIG. 13, the interfragmentary compression bone screw 170 is inserted into the second seating area 62. More particularly, the interfragmentary compression bone screw 170 is inserted generally along cross-plate axis 100. Upon installation, the inferior portion 174 of the screw head 172 engages the cowl abutment surface 96 and at least a portion of the curved side walls 72. Furthermore, upon installation, at least a portion of the screw head 172 may extend at least partially beneath a lower surface 58 of the bone plate 50. In this way, the screw head 172 may directly engage an inferior bone.

Figure 14:
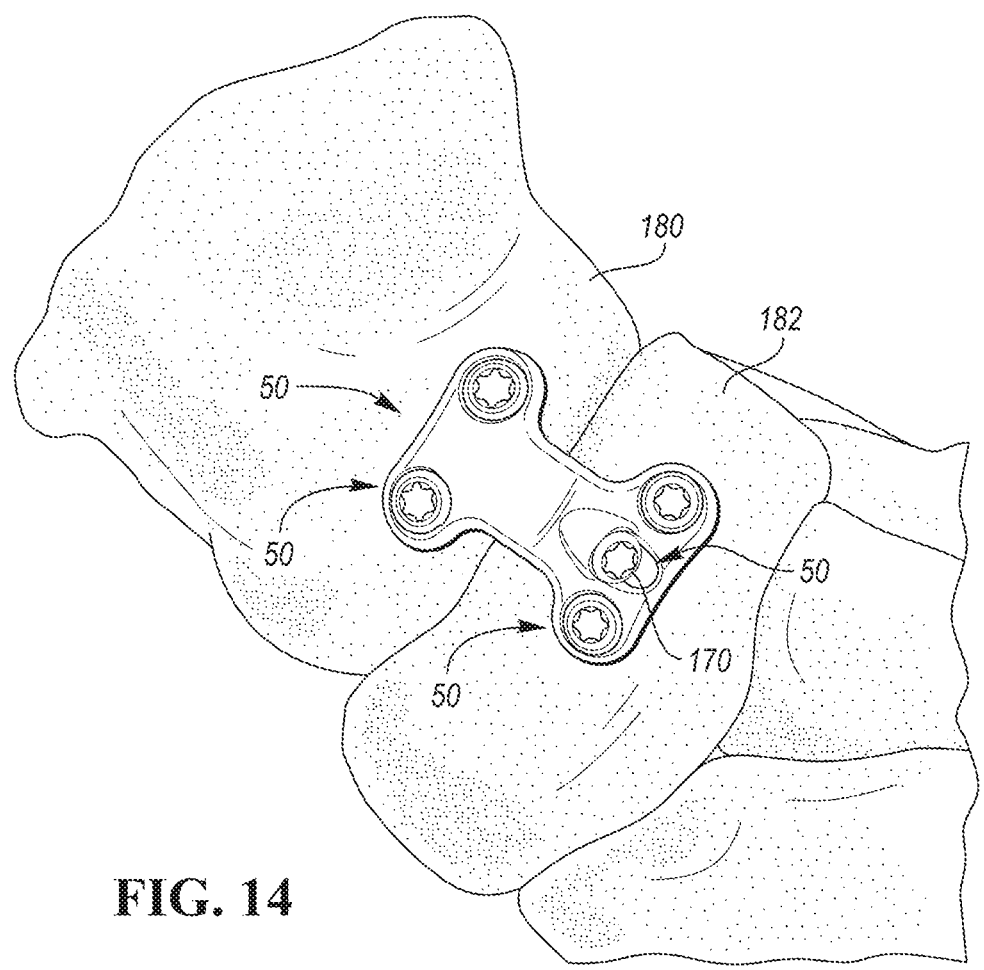
FIG. 14 is a perspective view of the first bone plate secured to a plurality of inferior bones.

Referring to FIG. 14, in the installed configuration, the bone plate 50 extends across the talus bone 180 of the hindfoot and the navicular bone 182 of the midfoot. The interfragmentary compression bone screw 170 installed in the combination hole structure 52 cooperates with additional bone screws installed in the locking hole structures 54 to thereby fuse the talus bone 180 and the navicular bone 182.

Figure 15:
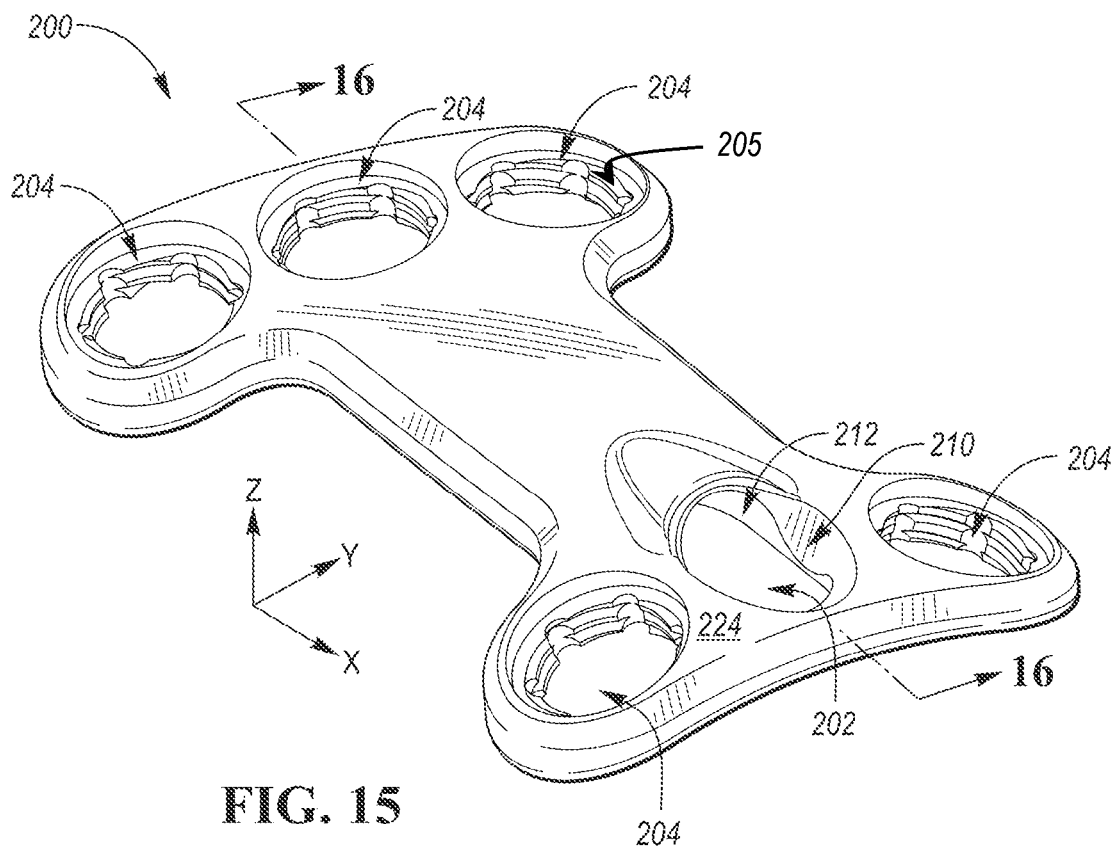
FIG. 15 is a top perspective view of a second bone plate.
Figure 16:
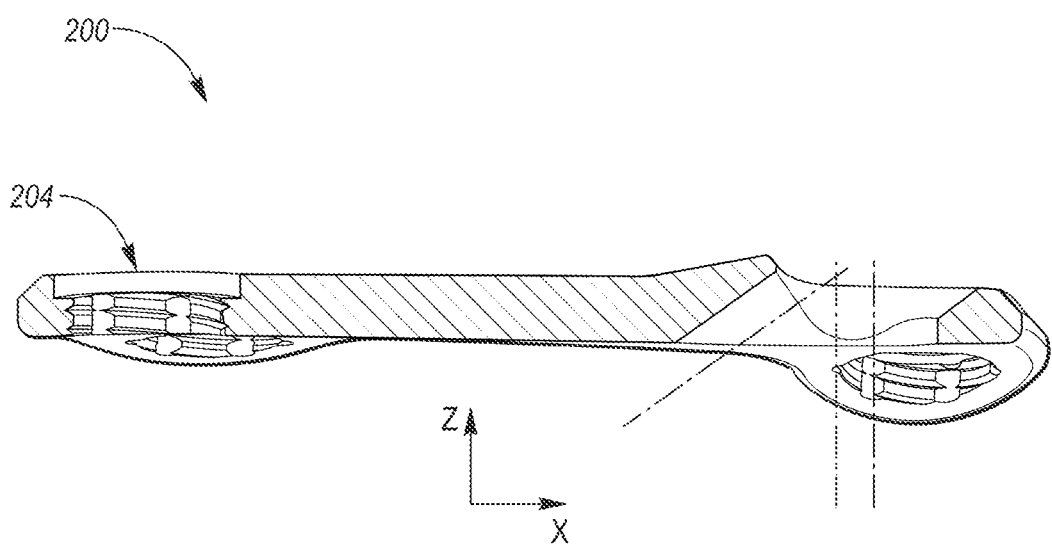
FIG. 16 is a cross-sectional view of the second bone plate taken along the line 16-16 of FIG. 15.

Turning now to FIGS. 15 and 16, a bone plate 200 with a first hole structure 202 is shown. The first hole structure 202 may generally correspond to the first hole structure 52 of FIGS. 4-9, and as such, may be referred to as a "combination" hole structure 202, or a "dual mode compression" hole structure.

The bone plate 200 may also include at least one second hole structure. For example, the depicted bone plate 200 includes five locking hole structures 204, including four locking hole structures 204 disposed through four lobes of the bone plate 200, and the fifth locking hole structure 204 disposed between two adjacent locking hole structures 204. The combination hole structure 202 extends through the bone plate 200 between the other two of the locking hole structures 204. The locking hole structures 204 include thread-engaging portions 205, which, in the illustrated embodiment, take the form of broken threads or lugs. Alternatively, these hole structures may include one or more interior unbroken threads (not shown). Furthermore, although shown as having common interior geometries, the locking hole structures 204 may have different interior geometries.

The bone plate 200 may be, for example, a naviculocuneiform plate that, following a surgical procedure, fuses the tarsal navicular bone with one or more of the medial, middle, and lateral cuneiforms.

The combination hole structure 202 may generally correspond to the combination hole structure 52 of bone plate 50. As such, the combination hole structure 202 permits a practitioner to choose among a plurality of bone screw varieties to be inserted into the combination hole structure 202. Similar to bone plate 50, a practitioner may opt to orient a first bone screw, such as the dynamic compression bone screw 150 of FIG. 10, at a first orientation through the combination hole structure 202, or may opt to orient a second bone screw, such as the interfragmentary compression bone screw 170 of FIG. 11, at a second orientation through the combination hole structure 202 that is different than the first orientation.

In this way, the combination hole structure 202 includes a first seating area, shown generally at 210, and a second seating area, shown generally at 212, that is at least partially offset from the first seating area 210. The first seating area 210 is configured to receive a dynamic compression screw, and the second seating area 212 is configured to receive an interfragmentary compression screw.

More particularly, the combination hole structure 202 includes a ramp wall 220, which may be referred to as an eccentric portion, and curved side walls 222 that extend about at least a portion of the first seating area 210. The ramp wall 220 and curved side walls 222 generally slope inwardly (e.g., toward a central axis of the combination hole structure 202) as the walls extend away from an upper surface 224 of the bone plate 200 in a direction of bone screw insertion (e.g., in a direction of the Z axis). In this way, the ramp wall 220 generally slopes in a direction toward the second seating area 212, and the curved side walls 222 generally slope toward each other.

As shown in FIG. 16, the ramp wall 220 may generally extend about a first axis, which may be referred to as an insertion axis 230, that extends in a direction of the Z axis. The curved side walls 222 may generally extend about a second axis. The second axis, which also extends in a direction of the Z axis, may be referred to as a seating axis 232. As shown, the seating axis 232 may be offset from the insertion axis 230; for example, along a direction of the X axis. The curved side walls 222 may cooperate to define a generally bowl-shaped first seating area 210. In this way, the curved side walls 222 may taper relative to the seating axis 232, and upper portions of the curved side walls 222 (e.g., proximate the upper surface 224) curve about the seating axis 232.

The bone plate 200 further includes a hood or cowl 240 that at least in part defines the second seating area 212. The cowl 240 includes an upper cowl surface 242 and a lower cowl surface 244 opposite the upper cowl surface 242. At least a portion of the upper cowl surface 242 is elevated (e.g., in the Z direction) relative to the upper surface 224 of the bone plate 200 proximate the curved side walls 222.

The cowl 240 may include a cowl abutment surface 246 that extends between the upper cowl surface 242 and the lower cowl surface 244. The cowl abutment surface 246 extends obliquely relative to one or both of the upper cowl surface 242 and the lower cowl surface 244.

As shown, the cowl 240 is contiguous with the curved side walls 222. More particularly, the cowl abutment surface 246 extends continuously from one or both of the curved side walls 222.

The lower cowl surface 244 extends about a cross-plate axis 250. The cross-plate axis 250 extends obliquely relative to one or both of the insertion axis 230 and the seating axis 232.

Figure 17:
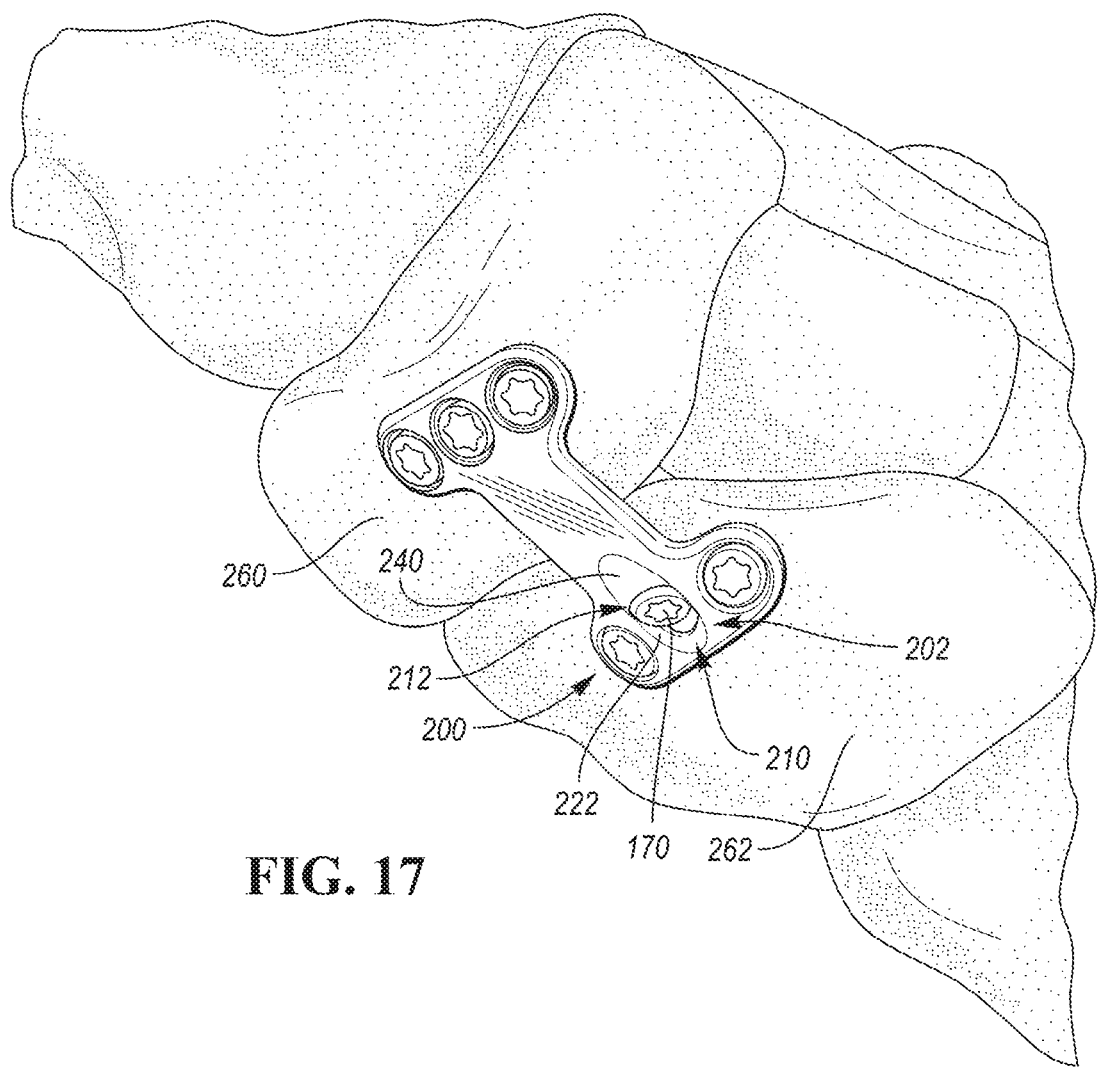
FIG. 17 is a perspective view of the second bone plate secured to a plurality of inferior bones.

Referring to FIGS. 16 and 17, the cowl 240 and the curved side walls 222 cooperate to facilitate insertion of an interfragmentary compression screw in the second seating area 212. As such, the interfragmentary compression bone screw 170 may be inserted into the second seating area 212. More particularly, the interfragmentary compression bone screw 170 is inserted generally along cross-plate axis 250. Upon insertion, the inferior portion 174 of the screw head 172 engages the cowl abutment surface 246.

Alternatively, as discussed, the combination hole structure 202 may facilitate insertion of a dynamic compression screw (not shown) through the first seating area 210 and into the inferior bone. More particularly, the ramp wall 220 and the curved side walls 222 cooperate to facilitate insertion of a dynamic compression bone screw 150 in the first seating area 210. The dynamic compression bone screw 150 may be initially inserted along insertion axis 230 such that the inferior portion 154 of the screw head 152 engages the ramp wall 220. As the dynamic compression bone screw 150 is driven into the bone (e.g., along a direction of the Z axis), the inferior portion 154 slides down the ramp wall 220, and concurrently slides horizontally (e.g., along a direction of the X axis) toward the seating axis 232.

In the installed configuration of FIG. 17, the bone plate 200 fuses the navicular bone 260 and one or more cuneiform bones 262. More particularly, the bone plate 200 extends across the navicular bone 260 and at least one of the cuneiform bones 262. The interfragmentary compression bone screw 170 is inserted through the first hole structure 202, and into both the navicular bone 260 and a cuneiform bone 262 to thereby fuse the two bones.

Figure 18:
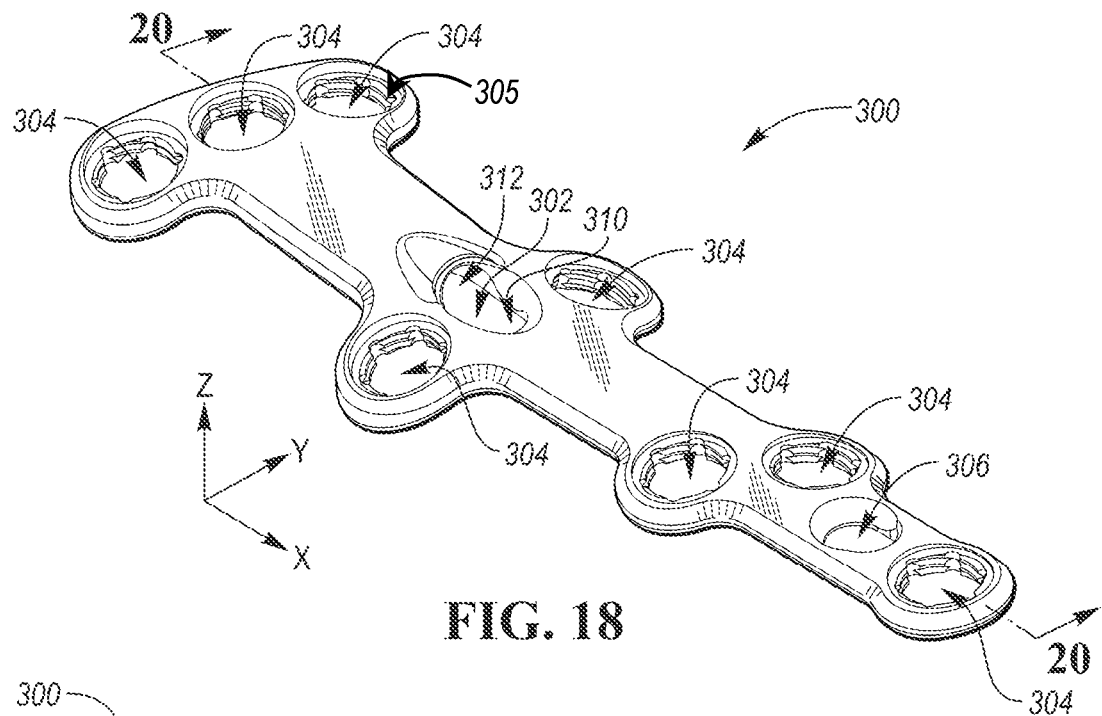
FIG. 18 is a top perspective view of a third bone plate.
Figure 19:
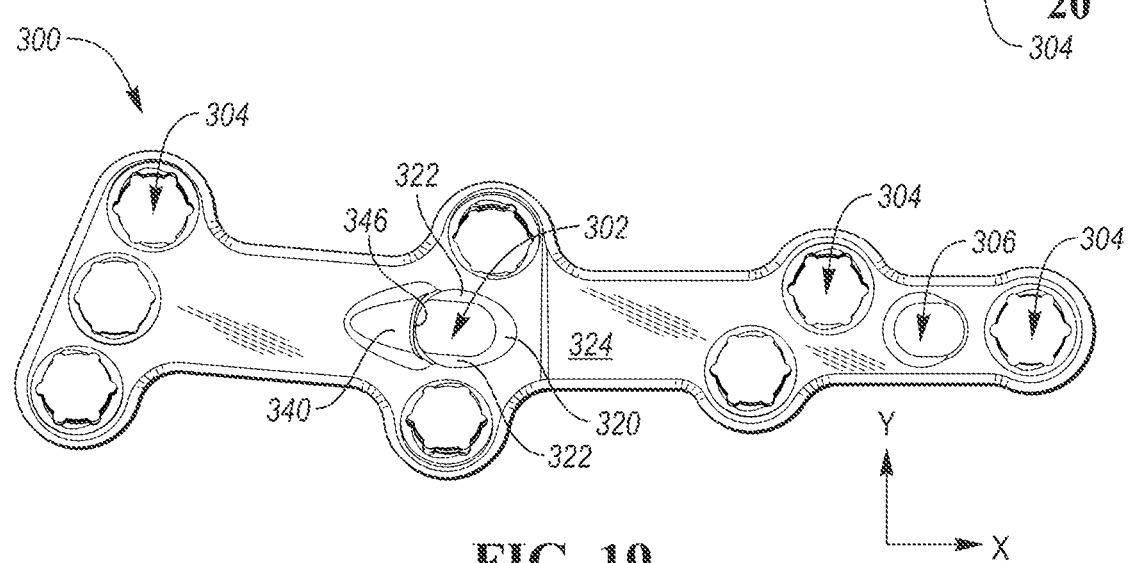
FIG. 19 is a top plan view of the third bone plate.
Figure 20:
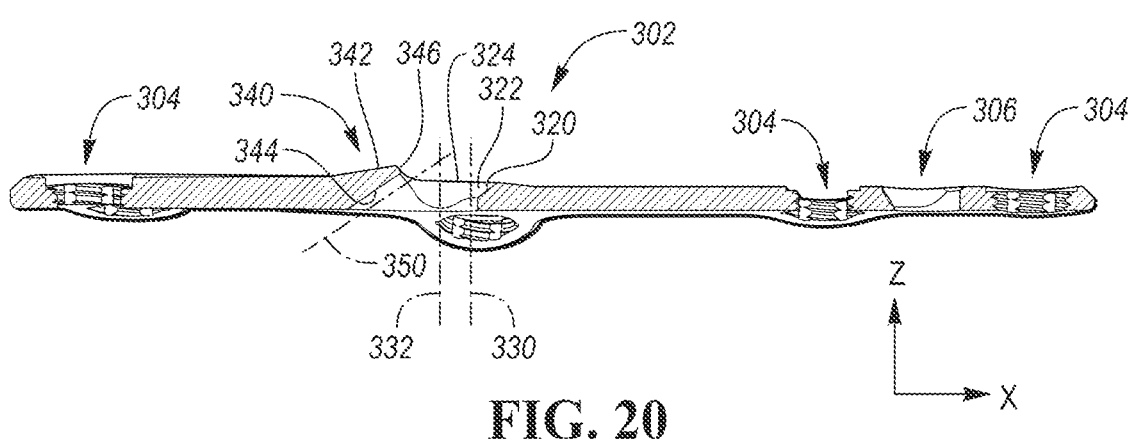
FIG. 20 is a cross-sectional view of the third bone plate taken along the line 20-20 of FIG. 18.
Figure 21:
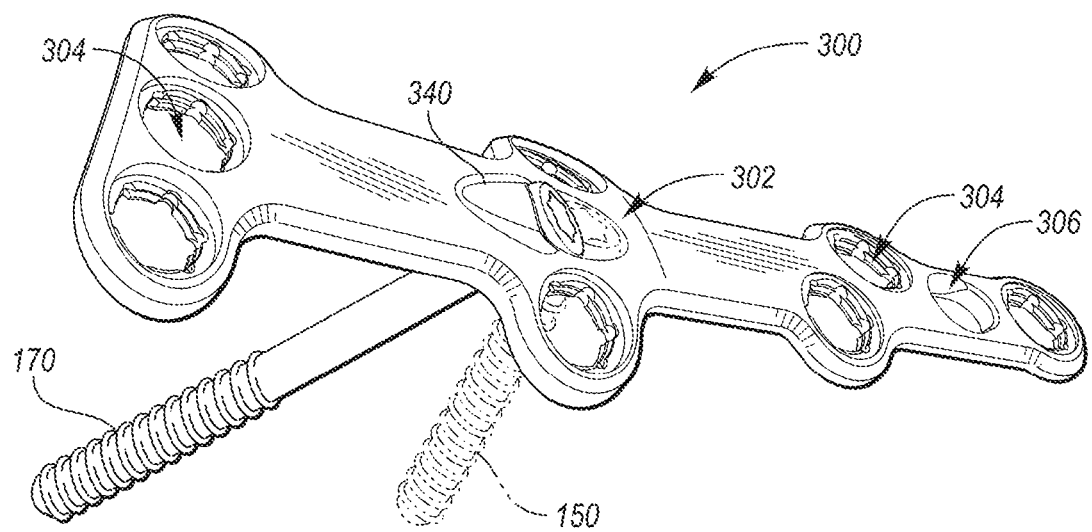
FIG. 21 is a top perspective view of the third bone plate showing the second bone screw of FIG. 11 assembled with the third bone plate, and alternatively as indicated by broken lines, the first bone screw of FIG. 10 assembled with the third bone plate.

Turning now to FIGS. 18-20, a bone plate 300 with a first hole structure 302 is shown. The first hole structure 302 may generally correspond to the first hole structure 52 of FIGS. 4-9, and as such, may be referred to as a "combination" hole structure 202, or a "dual mode compression" hole structure.

The bone plate 300 may also include at least one second hole structure. For example, the depicted bone plate 300 includes eight locking hole structures 304, including seven locking hole structures 204 disposed through seven lobes of the bone plate 300, and an eighth locking hole structure 204 disposed between two adjacent locking hole structures 304. The combination hole structure 302 extends through the bone plate 300 between two of the intermediate locking hole structures 304. The locking hole structures 304 include thread-engaging portions 305, which, in the illustrated embodiment, take the form of broken threads or lugs. Alternatively, these hole structures may include one or more interior unbroken threads (not shown). Furthermore, although shown as having common interior geometries, the locking hole structures 304 may have different interior geometries.

The bone plate 300 may further include at least one dedicated dynamic compression hole structure 306.

The bone plate 300 may be, for example, a medial column fusion plate that, following a surgical procedure, fuses the tarsal navicular bone with a cuneiform bone as well as with a metatarsal bone.

The combination hole structure 302 may generally correspond to the combination hole structure 52 of bone plate 50. As such, the combination hole structure 302 permits a practitioner to choose among a plurality of bone screw varieties to be inserted into the combination hole structure 302. Similar to bone plate 50, a practitioner may opt to orient a first bone screw, such as the dynamic compression bone screw 150 of FIG. 10, at a first orientation through the combination hole structure 302, or may opt to orient a second bone screw, such as the interfragmentary compression bone screw 170 of FIG. 11, at a second orientation through the combination hole structure 302 that is different than the first orientation.

In this way, the combination hole structure 302 includes a first seating area, shown generally at 310, and a second seating area, shown generally at 312, that is at least partially offset from the first seating area 310. The first seating area 310 is configured to receive a dynamic compression screw, and the second seating area 312 is configured to receive an interfragmentary compression screw.

More particularly, the combination hole structure 302 includes a ramp wall 320, which may be referred to as an eccentric portion, and curved side walls 322 that extend about at least a portion of the first seating area 310. The ramp wall 320 and curved side walls 322 generally slope inwardly (e.g., toward a central axis of the combination hole structure 302) as the walls extend away from an upper surface 324 of the bone plate 300 in a direction of bone screw insertion (e.g., in a direction of the Z axis). In this way, the ramp wall 320 generally slopes in a direction toward the second seating area 312, and the curved side walls 322 generally slope toward each other.

As shown in FIG. 20, the ramp wall 320 may generally extend about a first axis, which may be referred to as an insertion axis 330, that extends orthogonal to the X-Y plane. The curved side walls 322 may generally extend about a second axis. The second axis, which also extends orthogonal to the X-Y plane, may be referred to as a seating axis 332.

As shown, the seating axis 332 may be offset from the insertion axis 330; for example, along a direction of the X axis. The curved side walls 322 may cooperate to define a generally bowl-shaped first seating area 310. In this way, the curved side walls 322 may taper relative to the seating axis 332, and upper portions of the curved side walls 322 (e.g., proximate the upper surface 324) curve about the seating axis 332.

The bone plate 300 further includes a hood or cowl 340 that at least in part defines the second seating area 312. The cowl 340 includes an upper cowl surface 342 and a lower cowl surface 344 opposite the upper cowl surface 342. At least a portion of the upper cowl surface 342 is elevated (e.g., in the Z direction) relative to the upper surface 324 of the bone plate 300 proximate the curved side walls 322.

The cowl 340 may include a cowl abutment surface 346 that extends between the upper cowl surface 342 and the lower cowl surface 344. The cowl abutment surface 346 extends obliquely relative to one or both of the upper cowl surface 342 and the lower cowl surface 344.

As shown, the cowl 340 is contiguous with the curved side walls 322. More particularly, the cowl abutment surface 346 extends continuously from one or both of the curved side walls 322.

The lower cowl surface 344 extends about a cross-plate axis 350. The cross-plate axis 350 extends obliquely relative to one or both of the insertion axis 330 and the seating axis 332.

Referring to FIGS. 18-21, the cowl 340 and the curved side walls 322 cooperate to facilitate insertion of an interfragmentary compression bone screw 170 in the second seating area 312. More particularly, the interfragmentary compression bone screw 170 is inserted generally along cross-plate axis 350. Upon insertion, the inferior portion 174 of the screw head 172 engages the cowl abutment surface 346.

Alternatively, as discussed, the combination hole structure 302 may facilitate insertion of a dynamic compression bone screw 150 through the first seating area 310 and into an inferior bone. More particularly, the ramp wall 320 and the curved side walls 322 cooperate to facilitate insertion of a dynamic compression screw in the first seating area 310. As such, the dynamic compression bone screw 150 may be initially inserted along insertion axis 330 such that the inferior portion 154 of the screw head 152 engages the ramp wall 320. As the dynamic compression bone screw 150 is driven into the bone (e.g., along a direction of the Z axis), the inferior portion 154 slides down the ramp wall 320, and concurrently slides horizontally (e.g., along a direction of the X axis) toward the seating axis 332.

Figure 22:
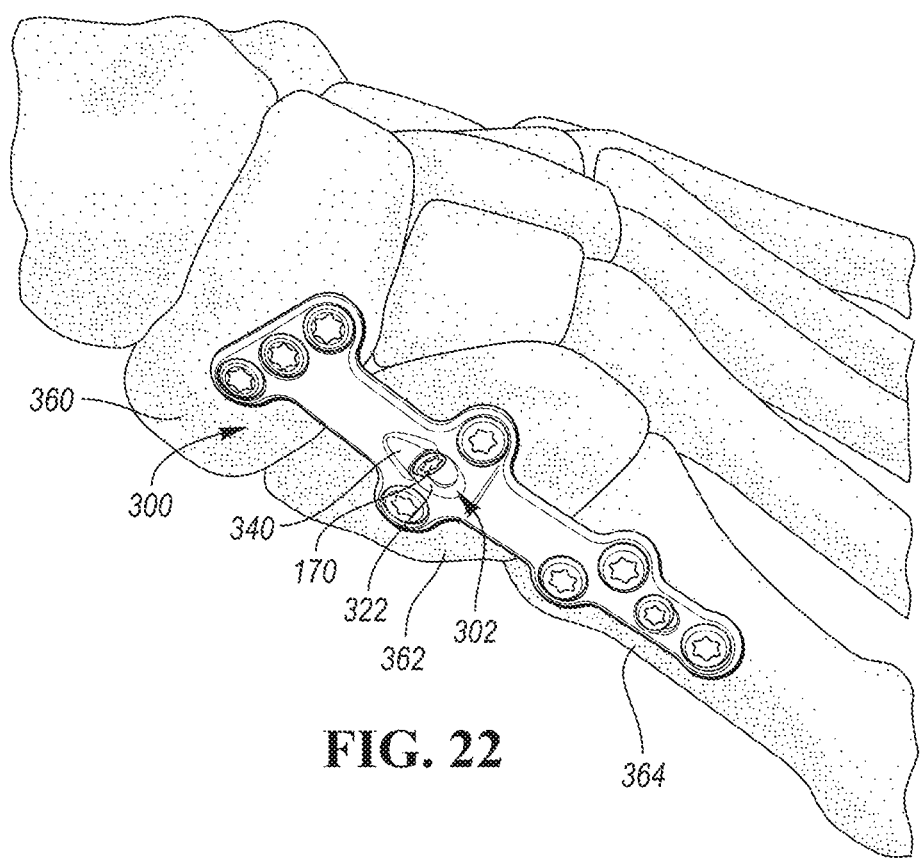
FIG. 22 is a perspective view of the third bone plate secured to a plurality of inferior bones.

In the installed configuration of FIG. 22, the bone plate 300 fuses the tarsal navicular bone 360 with a cuneiform bone 362 as well as with a metatarsal bone 364. More particularly, the bone plate 300 extends across the navicular bone 360, across at least one of the cuneiform bones 362, and across a metatarsal bone 364. The interfragmentary compression bone screw 170 is inserted through the first hole structure 302, and into both the navicular bone 360 and a cuneiform bone 362 to thereby fuse the two bones.

Figure 23:
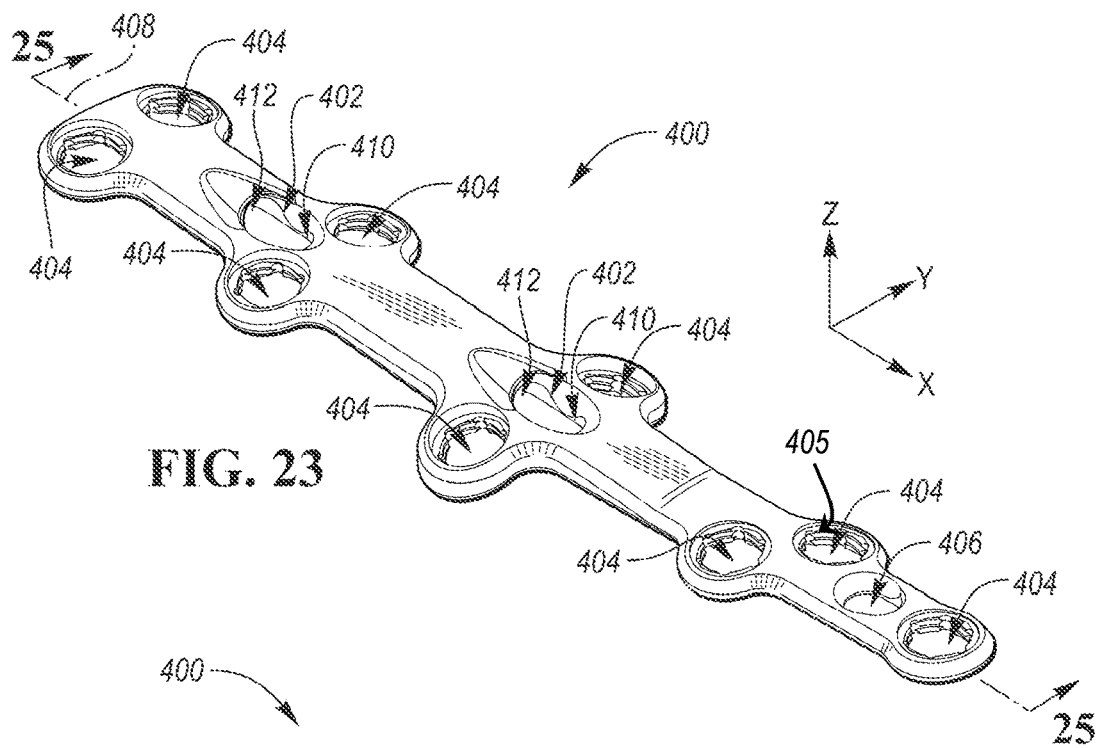
FIG. 23 is a top perspective view of a fourth bone plate.
Figure 24:
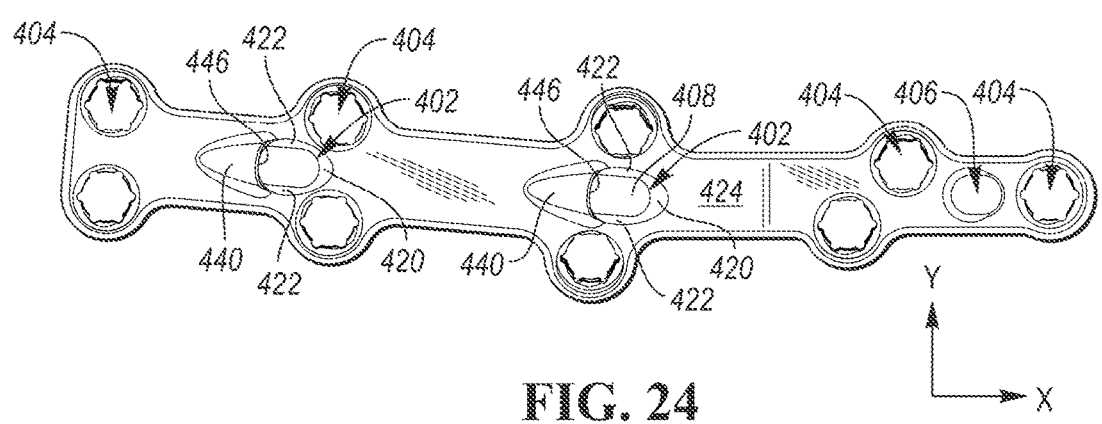
FIG. 24 is a top plan view of the fourth bone plate.
Figure 25:
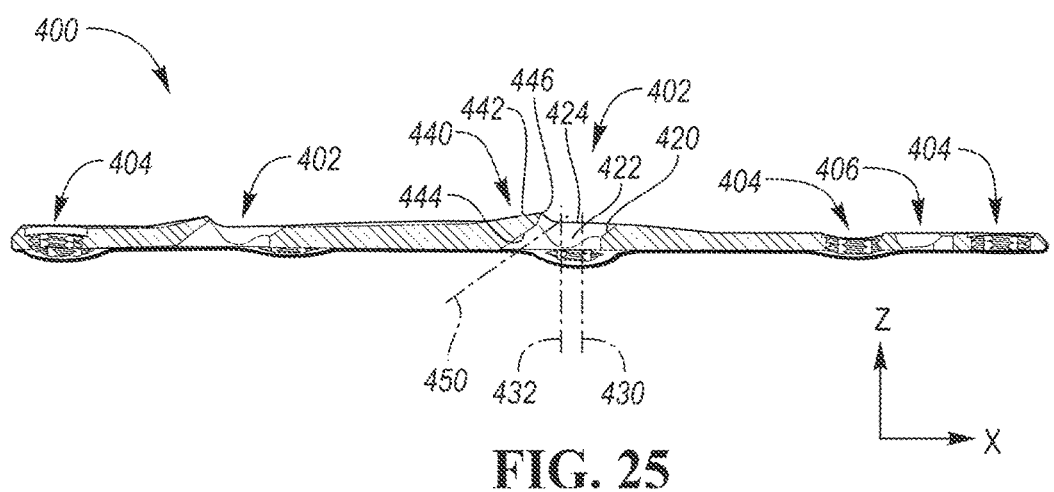
FIG. 25 is a cross-sectional view of the fourth bone plate taken along the line 25-25 of FIG. 23.

Turning now to FIGS. 23-25, a bone plate 400 with a first hole structure 402 is shown. The first hole structure 402 may generally correspond to the first hole structure 52 of FIGS. 4-9, and as such, may be referred to as a "combination" hole structure 402, or a "dual mode compression" hole structure. In the approach shown, the bone plate 400 includes two combination hole structures 402 that are spaced apart along a longitudinal axis 408 of the bone plate 400.

The bone plate 400 may also include at least one second hole structure. For example, the depicted bone plate 400 includes nine locking hole structures 404. The locking hole structures 404 include thread-engaging portions 405, which, in the illustrated embodiment, take the form of broken threads or lugs. Alternatively, these hole structures may include one or more interior unbroken threads (not shown). Furthermore, although shown as having common interior geometries, the locking hole structures 404 may have different interior geometries.

The bone plate 400 may further include at least one dedicated dynamic compression hole structure 406.

The bone plate 400 may be, for example, a medial column fusion plate that, following a surgical procedure, fuses the tarsal navicular bone with a cuneiform bone as well as with a metatarsal bone.

The combination hole structure 402 may generally correspond to the combination hole structure 52 of bone plate 50. As such, the combination hole structure 402 permits a practitioner to choose among a plurality of bone screw varieties to be inserted into the combination hole structure 402. Similar to bone plate 50, a practitioner may opt to orient a first bone screw, such as the dynamic compression bone screw 150 of FIG. 10, at a first orientation through the combination hole structure 402, or may opt to orient a second bone screw, such as the interfragmentary compression bone screw 170 of FIG. 11, at a second orientation through the combination hole structure 402 that is different than the first orientation.

In this way, the combination hole structure 402 includes a first seating area, shown generally at 410, and a second seating area, shown generally at 412, that is at least partially offset from the first seating area 410. The first seating area 410 is configured to receive a dynamic compression screw, and the second seating area 412 is configured to receive an interfragmentary compression screw.

More particularly, the combination hole structure 402 includes a ramp wall 420, which may be referred to as an eccentric portion, and curved side walls 422 that extend about at least a portion of the first seating area 410. The ramp wall 420 and curved side walls 422 generally slope inwardly (e.g., toward a central axis of the combination hole structure 402) as the walls extend away from an upper surface 424 of the bone plate 400 in a direction of bone screw insertion (e.g., in a direction of the Z axis). In this way, the ramp wall 420 generally slopes in a direction toward the second seating area 412, and the curved side walls 422 generally slope toward each other.

As shown in FIG. 25, the ramp wall 420 may generally extend about a first axis, which may be referred to as an insertion axis 430, that extends orthogonal to the X-Y plane. The curved side walls 422 may generally extend about a second axis. The second axis, which also extends orthogonal to the X-Y plane, may be referred to as a seating axis 432. As shown, the seating axis 432 may be offset from the insertion axis 430; for example, along a direction of the X axis. The curved side walls 422 may cooperate to define a generally bowl-shaped first seating area 410. In this way, the curved side walls 422 may taper relative to the seating axis 432, and upper portions of the curved side walls 422 (e.g., proximate the upper surface 424) curve about the seating axis 432.

The bone plate 400 further includes a hood or cowl 440 that at least in part defines the second seating area 412. The cowl 440 includes an upper cowl surface 442 and a lower cowl surface 444 opposite the upper cowl surface 442. At least a portion of the upper cowl surface 442 is elevated (e.g., in the Z direction) relative to the upper surface 424 of the bone plate 400 proximate the curved side walls 422.

The cowl 440 may include a cowl abutment surface 446 that extends between the upper cowl surface 442 and the lower cowl surface 444. The cowl abutment surface 446 extends obliquely relative to one or both of the upper cowl surface 442 and the lower cowl surface 444.

As shown, the cowl 440 is contiguous with the curved side walls 422. More particularly, the cowl abutment surface 446 extends continuously from one or both of the curved side walls 422.

The lower cowl surface 444 extends about a cross-plate axis 450. The cross-plate axis 450 extends obliquely relative to one or both of the insertion axis 430 and the seating axis 432.

Referring to FIGS. 25-27, the cowl 440 and the curved side walls 422 cooperate to facilitate insertion of an interfragmentary compression bone screw 170 in the second seating area 412. More particularly, the interfragmentary compression bone screw 170 is inserted generally along cross-plate axis 450. Upon insertion, the inferior portion 174 of the screw head 172 engages the cowl abutment surface 446.

Alternatively, as shown in FIGS. 26 and 28, the combination hole structure 402 may facilitate insertion of a dynamic compression bone screw 150 through the first seating area 410 and into an inferior bone. More particularly, the ramp wall 420 and the curved side walls 422 cooperate to facilitate insertion of a dynamic compression screw in the first seating area 410. As such, the dynamic compression bone screw 150 may be initially inserted along insertion axis 430 such that the inferior portion 154 of the screw head 152 engages the ramp wall 420. As the dynamic compression bone screw 150 is driven into the bone (e.g., along a direction of the Z axis), the inferior portion 154 slides down the ramp wall 420, and concurrently slides horizontally (e.g., along a direction of the X axis) toward the seating axis 432.

In an installed configuration, the bone plate 400 fuses the tarsal navicular bone with a cuneiform bone as well as with a metatarsal bone. More particularly, the bone plate 400 extends across the navicular bone, across at least one of the cuneiform bones, and across a metatarsal bone. The interfragmentary compression bone screw 170 is inserted through the first hole structure 402, and into both the navicular bone and a cuneiform bone to thereby fuse the two bones.

The bone plate 400 may receive a multiple compression screws. For example, as shown in FIG. 26, the bone plate 400 may receive a dynamic compression bone screw 150 through a first combination hole structure 402, and may receive an interfragmentary compression bone screw 170 through a second combination hole structure 402. Other combinations are expressly contemplated. For example, the bone plate 400 may receive a first dynamic compression bone screw 150 through a first combination hole structure 402, and may receive a second dynamic compression bone screw 150 through a second combination hole structure 402. Alternatively, the bone plate 400 may receive a first interfragmentary compression bone screw 170 through a first combination hole structure 402, and may receive a second interfragmentary compression bone screw 170 through a second combination hole structure 402. A bone plate such as bone plate 400 having multiple combination hole structures 402 may be utilized, for example, when addressing compound fractures.

A kit comprises a bone plate as described herein and at least one bone screw, the screw being sized to seat in the combination hole and sized to enable cross-screw compression of an inferior fusion area. The length of the screw should be selected to cross the inferior fusion area when positioned for cross-screw compression. The length of the screw may be greater than 75% of the extent of the lateral distance between the centers of the combination hole and an opposing second hole that is positioned for cross-screw compression. The length may be greater than 80%, greater than 85%, greater than 90%, greater than 95%, or greater than 100% of this distance. The kit preferably includes additional bone screws, one screw for each hole in the bone plate. The screws all may be of identical size or the screws for the conventional holes in the bone plate may be sized differently from the screw that is intended for use with the combination hole. In some embodiments a longer screw may be used for cross-screw compression than for dynamic compression.

In use, a surgeon may determine whether to employ dynamic compression or cross-screw compression and will make the selection of which screw position to employ accordingly. The surgeon may make this determination prior to surgery or even during surgery when the surgeon has a better view of the inferior fusion area. The surgeon may then position a bone screw in either of the heretofore described positions and orientations to enable either dynamic or cross-screw compression of inferior bone structure. The bone plate system may be used to fuse a fracture or to fuse separate bones, or for other suitable purposes.

The bone plates described herein may be made of titanium or any suitable material, as may be the screws, and may be manufactured via conventional machining operations.

All methods described herein can be performed in any suitable order unless otherwise indicated herein or otherwise clearly contradicted by context. The use of any and all examples, or language describing an example (e.g., "such as") provided herein, is intended to illuminate the invention and does not pose a limitation on the scope of the invention. Any statement herein as to the nature or benefits of the invention or of the preferred embodiments is not intended to be limiting. This invention includes all modifications and equivalents of the subject matter recited herein as permitted by applicable law. Moreover, any combination of the above-described elements in all possible variations thereof is encompassed by the invention unless otherwise indicated herein or otherwise clearly contradicted by context. The description herein of any reference or patent, even if identified as "prior," is not intended to constitute a concession that such reference or patent is available as prior art against the present invention. No unclaimed language should be deemed to limit the invention in scope. Any statements or suggestions herein that certain features constitute a component of the claimed invention are not intended to be limiting unless reflected in the appended claims. Neither the marking of the patent number on any product nor the identification of the patent number in connection with any service should be deemed a representation that all embodiments described herein are incorporated into such product or service.

What is claimed is:

1. A bone plate system comprising:
   at least a first bone screw; and
   a bone plate having at least first and second screw-receiving hole structures defining respectively a first hole and a second hole, at least the first hole structure including:
   an eccentric portion adjacent a first seating area, a head of the first bone screw being shaped to engage the eccentric portion and via camming action to bias bone in an inferior fusion area into dynamic compression as the first bone screw is advanced, the first bone screw being positioned at a first orientation when the first bone screw is seated in the first seating area, and a cowl portion that at least partially defines a second seating area, the second seating area being positioned with respect to the first seating area such that the first bone screw is positioned at a second orientation when the first bone screw is seated in the second seating area, the second orientation being different from the first orientation and the first bone screw being sized to enable cross-screw compression of an inferior fusion area;

the first bone screw being seatable in either the first seating area or the second seating area.

2. The bone plate system of claim 1 wherein the eccentric portion is a ramp surface that generally extends about an insertion axis.

3. The bone plate system of claim 2 wherein opposing bowl-shaped side walls extend continuously from the eccentric portion to the cowl portion.

4. The bone plate system of claim 1, further comprising a second bone screw.

5. The bone plate system of claim 1 wherein the first bone screw is sized to extend laterally greater than 75% of an extent of a lateral distance between centers of the first hole and the second hole.

6. The bone plate system of claim 1 wherein the first bone screw is sized to extend laterally greater than 100% of an extent of a lateral distance between centers of the first hole and the second hole.

7. The bone plate system of claim 1 wherein the bone plate includes a third hole and a fourth hole, each being adjacent the first hole orthogonal a plane formed by the first and second orientations formed by the first bone screw.

8. The bone plate system of claim 1 wherein the second hole structure includes thread-engaging portions.

9. A bone plate system comprising:
a first screw;
a second screw; and
a bone plate having a hole structure for receiving the first screw for dynamic compression and the second screw for interfragmentary compression, the hole structure including:
a substantially smooth eccentric portion adjacent a first seating area, a head of the first screw being shaped to engage the substantially smooth eccentric portion and via camming action to bias bone in an inferior fusion area into dynamic compression as the first screw is advanced, the first screw being positioned at a first orientation when the first screw is seated in the first seating area, and a cowl portion that at least partially defines a second seating area, the second seating area being positioned with respect to the first seating area such that the second screw is positioned at a second orientation when the second screw is seated in the second seating area, the second orientation being different from the first orientation.

10. The bone plate system of claim 9 wherein the hole structure includes opposing bowl-shaped side walls that generally extend about an insertion axis and a seating axis that is offset from the insertion axis to guide sliding of the dynamic compression screw along the substantially smooth eccentric portion from the insertion axis to the seating axis.

11. The bone plate system of claim 9 wherein the hole structure includes side walls having first wall portions and second, generally bowl-shaped wall portions that extend upwardly from the first wall portions.

12. The bone plate system of claim 11 wherein the first wall portions are generally planar.

13. The bone plate system of claim 11 wherein opposing walls of the first wall portions are generally parallel.

14. The bone plate system of claim 9 wherein the cowl portion forms an abutment surface that extends continuously from the generally bowl-shaped wall portions.

15. The bone plate system of claim 9 wherein the cowl portion forms an abutment surface that extends obliquely relative to one or both of an upper cowl surface and a lower cowl surface.

16. The bone plate system of claim 9 wherein the hole structure forms a continuous width along bottom wall of the bone plate between the first and second seating areas.

17. The bone plate system of claim 9 wherein the hole structure generally forms an oval along bottom wall of the bone plate from the first seating area to the second seating area.

18. The bone plate system of claim 9 wherein the cowl portion continuously increases in thickness between an abutment surface of the cowl portion and a bottom wall of the bone plate.

19. The bone plate system of claim 9 wherein heads of the first screw and the second screw have a common shape for each seating in either the first seating area or the second seating area.

20. The bone plate system of claim 9 wherein the substantially smooth eccentric portion is unthreaded.

* * * * *